United States Patent [19]

Berg et al.

[11] Patent Number: 5,015,098

[45] Date of Patent: May 14, 1991

[54] DENSITOMETER WITH ERROR CORRECTION

[75] Inventors: Bernard J. Berg, Kentwood; David R. Bowden, Grand Rapids; Mark A. Cargill, Belding; William R. Given, Kentwood, all of Mich.

[73] Assignee: X-Rite, Incorporated, Grandville, Mich.

[21] Appl. No.: 534,205

[22] Filed: Jun. 7, 1990

Related U.S. Application Data

[63] Continuation of Ser. No. 105,424, Oct. 5, 1987, abandoned.

[51] Int. Cl.$^5$ .............................................. G01J 3/52
[52] U.S. Cl. .................................... 356/402; 356/419; 356/406
[58] Field of Search ............... 356/402, 406, 429, 405, 356/419

[56] References Cited

U.S. PATENT DOCUMENTS

| | | |
|---|---|---|
| 2,287,322 | 6/1942 | Nelson . |
| 3,322,025 | 5/1967 | Dauser . |
| 3,614,241 | 10/1971 | Acton et al. . |
| 4,003,660 | 1/1977 | Christie, Jr. et al. ............ 356/429 X |
| 4,055,813 | 10/1977 | French ................................. 330/103 |
| 4,125,329 | 11/1978 | French et al. ....................... 356/405 |
| 4,194,838 | 3/1980 | Bey et al. ............................. 356/404 |
| 4,239,393 | 12/1980 | Tobias .................................. 356/407 |
| 4,417,818 | 11/1983 | Weisner ............................... 356/404 |
| 4,654,794 | 3/1987 | O'Brien ............................... 364/413 |
| 4,773,761 | 9/1988 | Sugiyama et al. .................. 356/405 |

*Primary Examiner*—Vincent P. McGraw

*Attorney, Agent, or Firm*—Varnum, Riddering, Schmidt & Howlett

[57] ABSTRACT

A densitometer apparatus (200) is disclosed and is adapted to provide color density measurements of opaque materials. The densitometer apparatus (200) comprises a light source unit (202) having a source light (204) projecting light through a collimating lens (206). Light rays transmitted through the collimating lens (206) project through an aperture (208). The rays are projected onto an irradiated area surface of an object sample (212) under test. Electromagnetic radiation in the form of reflected light rays (214) are reflected from the sample (212). The reflected light rays are directed through a spectral filter apparatus (216) and impinge on receptor surfaces of photo-voltaic sensor cells (232, 234, 236). The sensors (232, 234, 236) generate electrical currents having magnitudes proportional to the intensities of the sensed light rays. The electrical signals are applied as input signals to amplifiers (244, 246, 248), with the amplified signals applied as input signals to a multiplexer (256) for time multiplexing each of the output signals from the amplifiers. The resultant multiplexed signal is applied as an input signal to an A/D converter (264) to convert the analog multiplexed signal to a digital signal. The digital output signal from the A/D converter (264) is applied as a parallel set of binary information signals to a central processing unit (266). Actual measurements of color reference patches are processed so as to solve for unknown constants of a set of equations representing correction or compensation factors functionally dependent on actual reflectance measurements. The correction factors are then utilized by the densitometer apparatus (200) to compensate measurements of actual object samples.

20 Claims, 6 Drawing Sheets

DENSITOMETER WITH ERROR CORRECTION

This is a continuation of application Ser. No. 07/105,424 filed Oct. 5, 1987, now abandoned.

TECHNICAL FIELD

The invention relates to densitometer apparatus and, more specifically, to densitometers having means for correcting measurement errors caused by spectral response deviations.

BACKGROUND OF THE INVENTION

It is well known that the term "color" as applied to electromagnetic radiation represents in part the relative energy distribution of the radiation within the visible spectrum. That is, light providing a stimulus to the human eye, and having a particular energy distribution, may be perceived as a substantially different color than light of another energy distribution. Concepts relating to the characteristics of color and light waves are the subjects of numerous well known texts, such as *Principles of Color Technology*, Billmeyer, Jr. and Saltzman (Wiley 1966).

In recent years, the capability of maintaining the "quality" of color has become of significant importance in various industries, such as, for example, the fields of graphic arts, photography and color film processing. With respect to the graphic arts fields, it is necessary, for example, to maintain appropriate color quality throughout a production run of a color printing sheet.

For purposes of performing sample testing and other activities in furtherance of maintaining color quality, it is necessary to first determine an appropriate means for "measuring" and "describing" color. A substantial amount of research has been performed during the past 50 years with respect to appropriate methods and standards for color measurement and description.

For purposes of describing color, and from a purely physical point of view, the production of color requires three things: a source of light, an object to be illuminated, and a means for perceiving the color of the object. The means for perceiving the color can be the human eye and brain or, alternatively, a photosensitive detector and associated auxiliary equipment utilized for detecting light.

The maintenance of quality standards in photography requires precise control of exposure, source intensity, development procedures and film characteristics, in addition to the control of environmental variables. Similarly, the maintenance of quality standards in graphic arts also involves consideration of some of the same parameters and variables. In general, it is desirable to provide a means for measuring color so as to assess the manner in which an image will appear to a human observer, or the manner in which an image will perform in a photographic or other type of reproduction printing operation.

One parameter widely used in the field of color technology for obtaining a quantitative measurement is typically characterized as optical "density." Described simplistically, when light is directed onto an object or object sample to be measured for color, the object may absorb a portion of the light energy while correspondingly passing through or reflecting (if the object is opaque) other portions of the light. The color characteristics of the object sample will depend in part on the spectral characteristics of the object. That is, the effect of an object on light can be described by its spectral transmittance or reflectance curves (for transparent or opaque materials, respectively). These spectral characteristic curves indicate the fraction of the source light at each wavelength transmitted by or reflected from the materials. Such curves are a means for describing the effect of an object on light in a manner similar to the use of a spectral energy distribution curve for describing the characteristics of a source of light.

For purposes of determining these spectral characteristics, a detector can be appropriately positioned to respond to the light transmitted through or reflected by the object sample. Such a detector can, for example, be in the form of a photovoltaic device. Such a device can produce a current output proportional to input light intensity over several orders of magnitude.

In accordance with conventional optical physics, it is known that the proportion of light incident to an object sample and absorbed by such a sample is independent of the light intensity. Accordingly, a quantitative indication of the spectral characteristics of an object sample can be defined as the transmittance or reflectance of the sample. That is, the transmittance of a substantially transparent object can be defined as the ratio of power transmitted over light power incident to the sample. Correspondingly, for an opaque object sample, the reflectance can be defined as the ratio of power reflected from the object over the incident light power. For collimated light, these ratios can be expressed in terms of intensities rather than power. Furthermore, because of the nature of transmittance/reflectance and the optical characteristics of the human eye, it is advantageous to express these ratios in logarithmic form. Accordingly, the optical density of an object sample is typically defined as the negative logarithm to base 10 of the transmittance or reflectance. In accordance with the foregoing, if an object sample absorbed 90% of the light incident upon it, and the object were opaque, the reflectance would ideally be 10%. The density of such a sample would then be characterized as unity. Correspondingly, if 99.9% of the light were absorbed, the reflectance would be 0.1% and the density would be 3. Similarly, the density of an "ideal" object reflecting 100% of the light incident upon it would be zero.

To provide a relative measurement of color, it is possible to utilize the principles of density determinations without requiring measurement or knowledge of the absolute values of total incident light intensity or reflectance. That is, for example, it is possible to obtain relative color measurements among a series of object samples by utilizing a particular geometric configuration of light, object sample and reflectance or transmittance detector for each measurement, and standardizing the measurements in some desired manner.

In brief summary, optical density is a measure of the modulation of light or other radiant flux by an object sample, such as a given area of printed ink-on-paper. Density measurements provide a means to assess the manner in which an image will appear to a human observer, or the way an image will perform in a printing operation. Density measurements can be utilized to produce sensitometric curves to evaluate various printing and reproduction characteristics, as well as utilization to control various photographic operations, such as film processing.

For purposes of measuring optical densities, it is well known to employ a device typically characterized as a densitometer. For purposes of further description of the background of the invention, additional discussion will be limited to principles associated with "reflection" densitometers, which are employed for optical density measurements of opaque objects. However, it should be emphasized that the principles of the invention are not limited to reflection densitometers, and can readily be applied to other types of devices (such as transmittance densitometers) employed for determining the spectral characteristics of various non-opaque materials.

Reflection densitometers are utilized in the graphic arts for performing a variety of functions. As an example, it is common to provide color printing sheets with color bar strips extending along an edge of the sheet. When such a printing sheet has been approved for production, the optical color density of the color bars can be determined with the densitometer. Thereafter, during production runs, the color bars on the edges of corresponding printed sheets can be checked with the densitometer, so as to assure that appropriate color densities are being maintained.

In addition, reflection densitometers can be employed in the area of photography. For example, such a densitometer can be utilized to determine the optical density of the brightest or "highlight" areas, and the darkest or "shadow" areas of of a subject to be photographed. Such values can be utilized in adjusting controls of the camera so as to assure appropriate exposure.

Still further, reflection densitometers can be conveniently employed in color film processing. It is common for color film manufacturers to provide test strips having color bars. If the test strips have been appropriately processed, the bars will have known densitometer readings. Such strips can then be utilized to check operating parameters of a film processing system, before the system is utilized to process the exposed film.

To assist in describing the principles of the invention, presently known techniques of measuring optical density can be illustrated by the schematic representation of a known reflection densitometer configuration 100 as shown in FIG. 1. Referring to the numerical references therein, the prior art reflection densitometer 100 includes a light source unit 102 having a source light 104. With respect to optical density measurements in photography and other industrial fields, various standards have been developed for densitometer illuminating light sources. For example, densitometer standards have previously been described in terms of a tungsten lamp providing an influx from a lamp operating at a Planckian distribution of 3000K. Other suggested standards have been developed by the American National Standards Institute ("ANSI") and the International Organization for Standardization ("ISO"). These light source densitometry standards are typically defined in terms of the spectral energy distribution of the illuminant.

The source light 104 is directed through a collimating lens 106 which acts to converge the electromagnetic radiation from the source light 104 into substantially parallel rays of light. The light rays transmitted through the lens 106 are further directed through an aperture 108. The dimensions of the aperture 108 will determine the size of the irradiated area of the object sample under test. Various standards have been defined for preferable sizes of the irradiated area. Ideally, the aperture 108 would be of a size such that the irradiance is uniform over the entire irradiated area. Current standards suggest that the size of the irradiated area should be such that irradiance measured at any point within the area is at least 90 percent of the maximum value.

The light rays transmitted through aperture 108 (illustrated as rays 110 in FIG. 1) are projected onto the irradiated area surface of the object sample 112 under test. The sample 112 may be any of numerous types of colored opaque materials. For example, in the printing industry, the sample 112 may be an ink-on-paper sample comprising a portion of a color bar at the edge of a color printing sheet. However, as will be apparent from the subsequent description herein, the principles of the invention are not limited to measurement of printed ink-on-paper.

As the light rays 110 are projected onto the object sample 112, electromagnetic radiation shown as light rays 114 will be reflected from the sample 112. For purposes of determining the relative proportions of light reflected from various object samples, it is necessary to obtain a quantitative measurement of this reflected light. However, it is undesirable (and substantially impossible) to measure all of the light reflected from the sample 112. Accordingly, standard detection configurations have been developed whereby reflected light is detected at a specific angle relative to the illumination light rays 110 projected normal to the plane of the object sample 112. More specifically, standards have been developed for detection of reflected light rays at an angle of 45° to the normal direction of the light rays 110.

For purposes of actual detection of the reflected light rays 114, a rotatable spectral filter apparatus 116 is provided. The filter apparatus 116 can include a series of filters 118, 120 and 122 which are employed for purposes of discriminating red, green and blue spectral responses, respectively. That is, each of the filters will tend to absorb light energy at frequencies outside of the bandwidth representative of the particular color hue of the filter. For example, the red filter 118 will tend to absorb all light rays except for those within the spectral bandwidth corresponding to a red hue and centered about a wavelength of approximately 610 nanometers (nms). By detecting reflected light rays only within a particular color hue bandwidth, and obtaining an optical density measurement with respect to the same, a "figure of merit" can be obtained with respect to the quality of the object sample coloring associated with that particular color hue.

It is apparent from the foregoing that the actual quantitative measurement of color density or reflectance is dependent in substantial part on the spectral transmittance characteristics of the filters. Accordingly, various well known standards have been developed with respect to spectral characteristics of densitometer filters. For example, one standard for densitometer filters is known as the ANSI Status T Color Response. The spectral response characteristics of filters meeting this standard are relatively wideband (in the range of 50 to 60 nanometer bandwidth) for each of the red, blue and green color hues. Other spectral response characteristic standards include, for example, what is known as G-Response, which is somewhat similar to Status T, but is somewhat more sensitive with respect to denser yellow hues. An E-Response represents a European response standard.

The spectral filter apparatus 116 shown in FIG. 1 includes not only the filters 118, 120 and 122, but is also shown as including a shaft 124 having one end connected to a "wheel" 126 on which the spectral filters are positioned and spaced apart. The other end of the shaft 124 is connected to a manually rotatable knob 128. In the actual mechanical configuration of the densitometer 100, the knob 128 would be made accessible to the user for purposes of manual rotation of the wheel 126 so as to selectively position the individual filters as desired. In FIG. 1, the red filter 118 is shown as being appropriately positioned for detecting the reflected light rays 114.

The spectral filters 118, 120 and 122 can be any of several specific types of spectral response filters. For example, the filters 118, 120 and 122 can comprise a series of conventional Wratten gelatin filters and infrared glass. However, various other types of filter arrangements can also be employed.

As further shown in FIG. 1, the portion of the reflected light rays 114 which pass through the filters of the spectral filter apparatus 116 (shown as light rays 130) impinge on a receptor surface of a photovoltaic sensor cell 132. The sensor 132 is a conventional photoelectric element adapted to detect the light rays 130 eminating through the particular one of the filters 118, 120 and 122 then positioned to receive the reflected light rays 114. The sensor 132 is further adapted to generate an electrical current on line pair 134, with the magnitude of the output line current being proportional to the intensity of the light rays 130 sensed by the sensor 132. Photoelectric elements suitable for use as sensor 132 are well known in the art and various types of commercially available sensors can be employed.

The sensor current output on line pair 134 is applied as an input signal to a conventional amplifier 136. The amplifier 136 serves to convert the electrical current signal on line pair 134 to an output voltage signal on line 138. The amplifier 136 can include gain adjustment circuitry (representatively shown as an adjustable resistance in FIG. 1) 139 for purposes of varying the output voltage to input current gain. For example, a standard may be defined for the densitometer density reading for a particular spectral filter for zero density level. Accordingly, the amplifier circuit 136 can be adjusted by means of the gain adjustment circuitry 139 so that the densitometer reading is appropriate for the standard.

The output voltage signal from the amplifier 136 on line 138 can be applied as an input signal to a logarithmic voltage converter 140. The logarithmic voltage converter 140 is adapted to provide an output on line 142 which corresponds to the optical density measurement for the object sample 112 and the particular configuration of the spectral filter arrangement 116. This optical density measurement may be in the form of the negative logarithm (to the base 10) of the ratio of the voltage signal on line 138 to a standardized voltage magnitude. This standardized voltage magnitude can be set to a value which the user wishes to have correspond to a zero optical density measurement. That is, if the output voltage on line 138 is equal in magnitude to this standardized value, the logarithmic computation provided by the logarithmic converter 140 would generate a density measurement on line 142 of zero.

Preferably, the logarithmic converter 140 also has gain adjustment circuitry 144. This gain adjustment circuitry 144 can be utilized to set the density "slope" sensitivity of the converter 140. As is well known in the art of densitometer circuit design, logarithmic converters can vary in their response characteristics to input voltages. The gain adjustment provides a means for adjusting the response characteristics.

The voltage output from the logarithmic voltage converter 140 on line 142 can be applied to any of numerous types of conventional display apparatus 146. The display apparatus 146 is utilized to provide a visual display to the user of the density measurement represented by the logarithmic converter output voltage on line 142.

Although the foregoing prior art densitometer 100 has been described with the logarithmic conversion and gain adjustment functions represented by discrete components, it will be apparent that such functions can clearly be performed by means of a digital computer or other computer apparatus.

As is well known in the art, densitometer apparatus must first be "calibrated" to provide a desired density response characteristic for a given set of spectral filters. In known systems, for example, and as briefly discussed in previous paragraphs, the "zero density" condition and the response "slope" for a particular densitometer and filter set can be provided as parameters manually inputted to the densitometer. For example, to provide what can be characterized as an "initial condition" of zero density for each individual spectral filter, an object sample comprising a "white" reference patch (representing substantial reflection) can then be measured for each of the individual filters. The densitometer gain adjustments can then be manually adjusted so as to provide a standardized densitometer reading for the patch. Correspondingly, with the logarithmic density measurement assumed to be linear, the "slope" of the densitometer response can be set by means of viewing a "black" patch (representing substantial absorption), and setting the densitometer reading to a standardized "maximum" for the patch measurement for each of the filters.

Although the foregoing represents a means for calibrating zero density level measurements and density slope sensitivity, the known systems employing these calibration procedures still suffer from several substantial disadvantages. First, when standards are provided for adjusting the density level readings for particular filter types, the standards assume an "ideal" filter. However, any physically realizable spectral filter arrangement will vary from the ideal. For example, in a conventional Wratten filter configuration, such errors may be within the range of ±5 nanometers. Such filter manufacturing errors can correspondingly result in errors as large as ±0.08 Density units in measurement of certain printed ink types. Such errors are critical, since desired industry inter-instrument agreement is within ±0.02 Density.

In addition, historical data regarding density measurements can be of primary importance, especially within the printing industry. That is, all printing being performed within a singular controlled environment should be capable of measurement by a number of densitometers in a manner so that the same results are achieved for identical measurements. However, if a series of conventional densitometers were utilized to measure the same color area, and were calibrated in accordance with the previously described procedures, the densitometers would not display identical measurement readings. Accordingly, if one densitometer had been used for an extensive period of time and had generated important historical printing data, such data would be substantially useless if the densitometer malfunctioned and a second densitometer instrument was subsequently utilized.

Problems associated with previously known calibration procedures result from several other considerations, in addition to the problems associated with manufacturing tolerances of spectral filter arrangements. For example, specification standards for various types of spectral filter arrangements call for certain types of light and color temperature, in addition to other illuminant parameters. However, manufacturing errors exist with respect to all physically realized illuminants. Furthermore, as a densitometer is used over a period of time, filament lamps will tend to drift. Still further, manufacturing errors will tend to exist with respect to photovoltaic detectors and other densitometer components. All of these factors result in problems associated with calibration based on standard spectral responses and the use of multiple densitometers for measuring color within a singular environment.

SUMMARY OF THE INVENTION

In accordance with the invention, a densitometer system is adapted for measuring color characteristics for a plurality of color shades of a substantially opaque object sample under test. The system includes light source means for generating light rays and directing the same onto the object sample. Means are responsive to reflected light rays reflected from the object sample for generating measured signals representative of the intensities of the reflected light rays. Processing means are provided for processing the measured signals so as to generate data signals indicative of the color characteristics. An improvement is provided wherein the processing means comprises means for generating solutions to at least one correction factor function relating desired color characteristic measurements to actual color characteristic measurement readings for a color shade. The correction factor function is a function of the measured signals representative of the intensities of the reflected light rays for at least two of the color shades.

The system also includes input means connected to the processing means for receiving input data representative of desired color characteristic readings of reference samples. The object samples under test include a plurality of reference samples of various of a plurality of color shades. A first one of the reference samples is a substantially reflective color shade, and a second one of the reference samples is a color shade of relatively high absorptance. The input means are adapted to receive first user input data representative of desired density levels of a first set of color shades for the first reference sample. The input means as further adapted to receive second user input data representative of desired density levels of a second set of color shades for the second reference sample. The processing means is responsive to the first user input data and the second user input data for setting slopes of color density responses of the system.

The input means is further adapted for receiving third user input data representative of desired density readings for specific color shades, when the densitometer system is made to read the reference samples of like color shades. The first one of the reference samples is a white reference sample, while the second one of the reference samples is a black reference sample. The reference samples also include cyan, magenta and yellow reference samples.

The correction factor function includes a series of constants and independent variables, where the independent variables comprise values of the measured signals representative of intensities of the reflected light rays for at least two of the plurality of color shades. The system further includes output means connected to the processing means for providing to the user output data representative of color characteristic data for the object samples under test. The processing means includes means for generating the output data in the form of the value of the actual color characteristic measurements for a particular color shade, multiplied by the correction factor function for the particular color shade, thereby providing error correction.

The means responsive to reflected light rays reflected from the object sample for generating measured signals representative of intensities of the reflected light rays include spectral filter means. The filter means are positioned at a predetermined angle relative to the direction of object illumination by the light source, and are responsive to light rays reflected from the object sample so as to discriminate a predetermined color shade set of spectral responses of the reflected light rays. Detection means are responsive to the light rays transmitted through the spectral filter means for generating, on separate paths, signals representative of the intensities of the transmitted light rays. Multiplexing means are connected to the detection means for time multiplexing the signals on the separate paths.

The series of constants for the correction factor function include a first constant for making the densitometer system generate a desired color density value for a particular color shade, when the reference sample of the same color shade is measured. A second constant is provided for making the densitometer system generate a desired color density value for the particular color shade when reference samples other than reference samples of the particular color shade are measured. A third constant is provided for making the densitometer system generate a desired color density value for the particular color shade, when the densitometer system is measuring samples of relatively low color densities. A fourth constant is also provided, for making the mathematical formula $(F_c + K_c (M/C) - K_1 (C/M))$ substantially equal to one when the densitometer system is measuring a reference sample of a substantially black color shade. $K_c$ is the first constant, $K_1$ is the second constant, $K_2$ is the third constant and $F_c$ is the fourth constant. M is an actual color characteristic measurement of a reference sample of one of the color shades, and C is an actual color characteristic measurement of a reference sample of another of the color shades.

Further in accordance with the invention, a method is provided which is adapted for use in a densitometer system for measuring color characteristics of object samples under test. The method is specifically adapted for error correction through utilization of a plurality of reference samples of varying color shades. The method includes the steps of entering input data into the densitometer system representative of desired color characteristic readings for the reference samples, and generating light rays and directing the same onto the reference samples.

The method further comprises generation of measured signals representative of intensities of reflected light rays reflected from the reference samples. The measured signals are processed so as to generate data signals indicative of the color characteristics of the reference samples. Solutions to at least one correction factor function are also generated. The correction factor function relates desired color characteristic measurements to actual color characteristic measurements for a color shade. The correction factor function is a function of the measured signals representative of intensities of the reflected light rays for at least two of the color shades.

The entry of input data includes entering of input data representative of desired color characteristic readings of a first set of the color shades for a first one of the reference samples. Input data is also entered which is representative of desired color characteristic readings of a second set of the color shades for a second one of the reference samples. Still further, input data is entered which is representative of color characteristic readings for specific color shades which are desired when the densitometer system is made to read reference samples of like color shades.

In use of the method, the first one of the reference samples is a color shade of relatively low density, while the second one of the reference samples is a color shade of relatively high density. The method further includes the steps of setting slopes of color density responses of the densitometer system in accordance with the input data representative of desired color characteristic readings of the first and second sets of color shades.

Further with respect to the method in accordance with the invention, the plurality of reference samples can include first, second, third, fourth and fifth reference samples, having first, second, third, fourth and fifth color shades, respectively. The first color shade is a substantially reflective color shade, while the second color shade is a color shade of relatively high absorptance. The entry of input data includes entering data representative of desired zero density levels of the second, third, fourth and fifth color shades for the first reference sample. Input data is also entered which is representative of density levels of the second, third, fourth and fifth color shades for the second reference sample.

Still further, input data is also entered which is representative of the desired density reading for the third color shade when the system is made to read the third reference sample. Correspondingly, additional input data is entered which is representative of the desired density readings for the third and fourth color shades, when the system is made to read the third and fourth reference samples, respectively.

The method also includes generating measured signals representative of intensities of reflected light rays reflected from an object sample under test. The measured signals are processed so as to generate data signals indicative of the actual color characteristic readings of the object sample under test. Output data is generated in the form of corrected color characteristic readings. The corrected readings comprise the values of the actual color characteristic readings multiplied by the correction factor function.

BRIEF DESCRIPTION OF THE DRAWINGS

The background art pertaining to the invention has been previously described with reference to the drawings in which.

Figure 2:
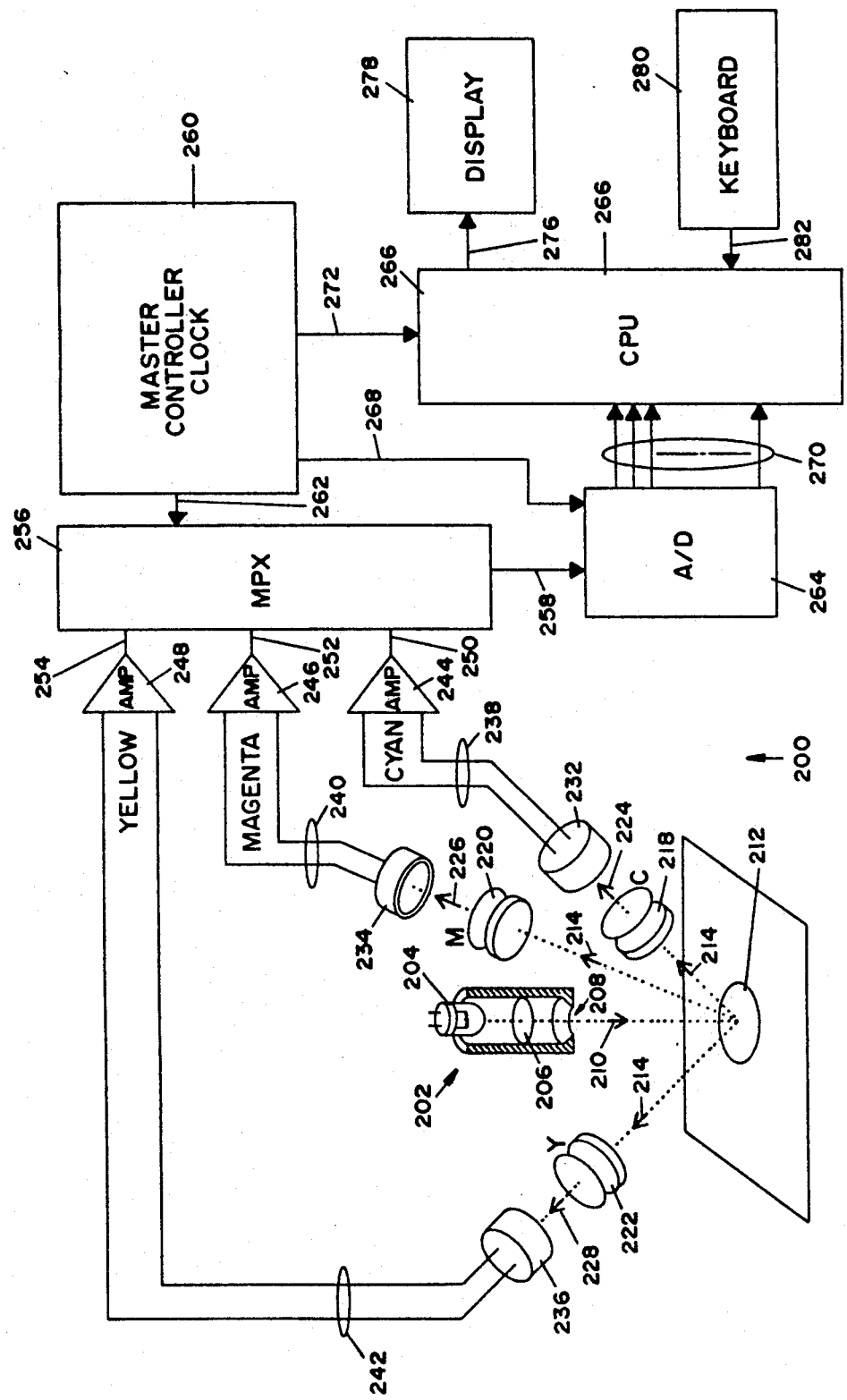
Figure 3:
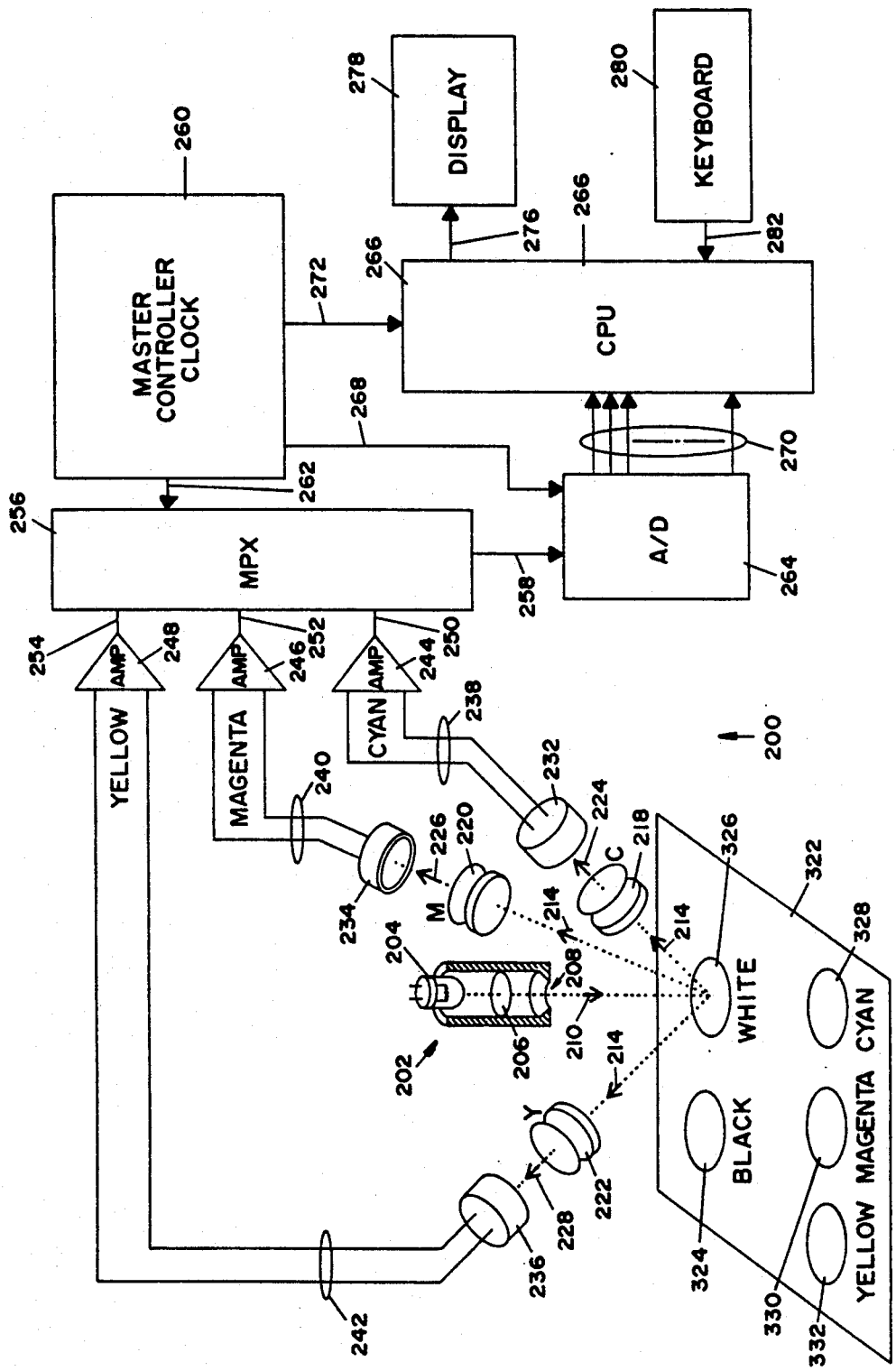
Figure 4:
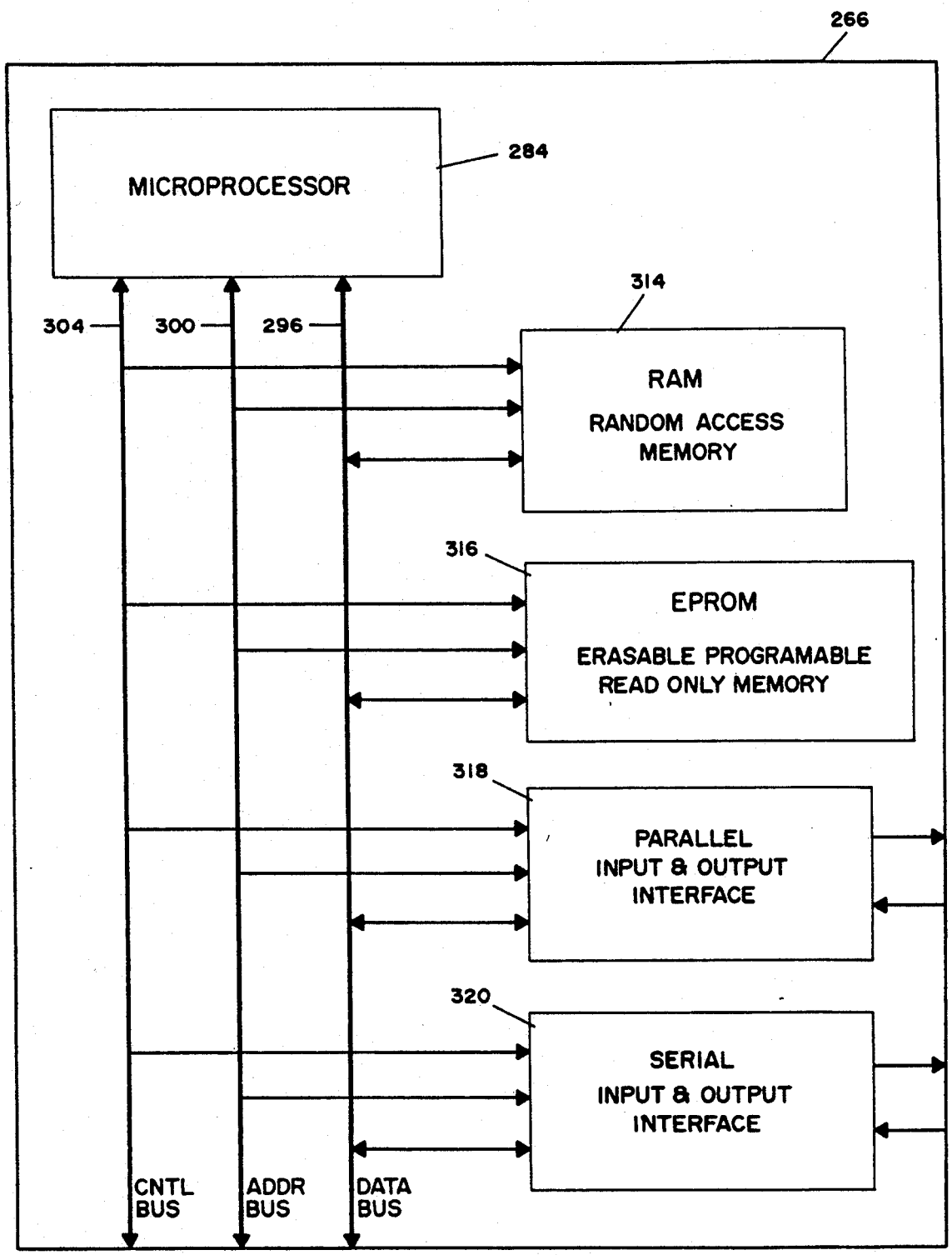
Figure 5:
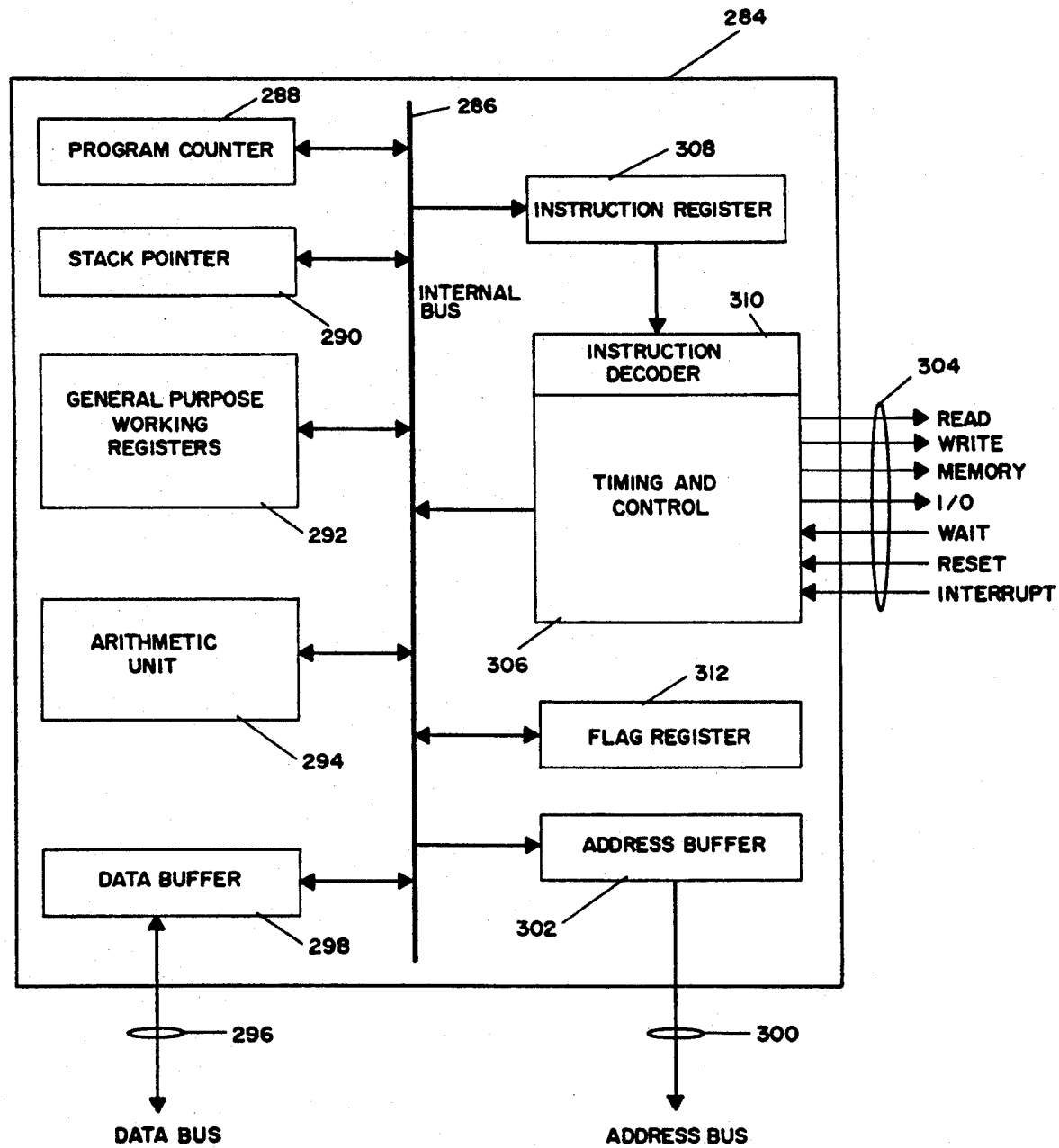
Figure 6:
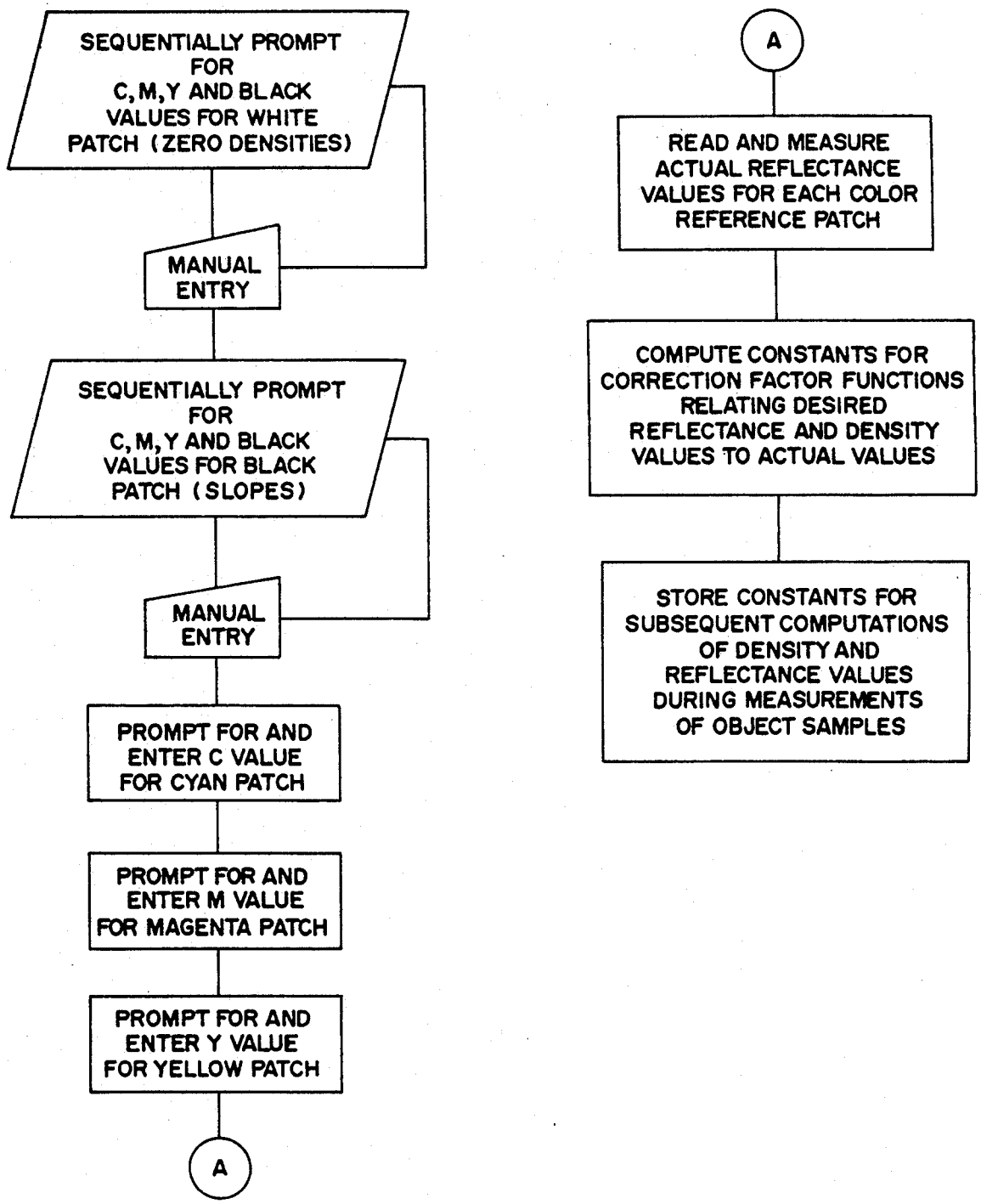

The invention will now be described with reference to the drawings in which:

FIG. 2 is a partially schematic block diagram of a densitometer apparatus in accordance with the invention;

FIG. 3 is a partially schematic block diagram of the densitometer apparatus shown in FIG. 2, with the addition of a color reference card;

FIG. 4 is a schematic block diagram of one illustrative embodiment of the central processing unit of the densitometer apparatus depicted in FIG. 2;

FIG. 5 is a schematic block diagram of one illustrative embodiment of a microprocessor which can be utilized in the central processing unit of the densitometer apparatus depicted in FIG. 2; and FIG. 6 depicts an illustrative embodiment of a sequence diagram illustrating an operational sequence for purposes of performing certain of the calibration functions of the densitometer apparatus in accordance with the invention.

DETAILED DESCRIPTION

The principles of the invention are disclosed, by way of example, in a densitometer apparatus 200 as depicted in FIG. 2 and described with respect to FIGS. 2-6. Densitometer apparatus of the type shown in FIG. 2 are characterized as reflection densitometers and utilized to provide color density measurements of opaque materials as previously described in the section entitled "Background of the Invention." In accordance with the invention, the densitometer apparatus 200 provides a means for correction of density measurement readings caused by spectral filter response deviations from standard spectral responses, in addition to correction of errors resulting from other component manufacturing tolerance deviations and deviations resulting from continuing use.

Several of the elements of the densitometer apparatus 200 were previously described with respect to the conventional densitometer configuration 100, and will only briefly be described herein. Referring specifically to FIG. 2, and the numerical references therein, the densitometer apparatus 200 includes a light source unit 202 having a source light 204. Various standards have been developed for densitometer light source illuminants for optical density measurements in photography, printing and other industrial fields. For example, densitometer standards have previously been described in terms of a tungsten lamp providing an influx from a lamp operating at a Planckian distribution of 3000K. Other suggested standards have been developed by the American National Standards Institute (ANSI) and the International Organization for Standardization ("ISO"). These source light densitometry standards are typically defined in terms of the spectral energy distribution of the illuminant. The source light 204 preferably conforms to an appropriate standard and can, for example, comprise a filament bulb meeting a standard conventionally known in the industry as 2856K ANSI. Power for the source light 204 and other elements of the densitometer apparatus 200 can be provided by means of conventional rechargeable batteries or, alternatively, interconnection to AC utility power.

The source light 204 projects light through a collimating lens 206 which serves to focus the electromagnetic radiation from the source light 204 into a narrow collimated beam of light rays. Various types of conventional and well-known collimating lenses can be employed. The light rays transmitted through the collimating lens 206 project through an aperture 208. The dimensions of the aperture 208 will determine the size of the irradiated area of the object sample under test. Various standards have been defined for preferable sizes of the irradiated area. Ideally, the aperture 208 is of a size such that the irradiance is uniform over the entire irradiated area. However, in any physically realizable densitometer arrangement, such uniform irradiance cannot be achieved. Current standards suggest that the size of the irradiated area should be such that irradiance measured at any point within the area is at least 90 percent of the maximum value. In addition, however, aperture size is typically limited to the size of color bar areas to be measured, and is also sized so as to reduce stray light.

The light rays emerging from the aperture 208 (illustrated as rays 210 in FIG. 2) are projected onto the irradiated area surface of an object sample 212 under test. The sample 212 may be any of numerous types of colored opaque materials. For example, in the printing industry, the sample 212 may be an ink-on-paper sample comprising a portion of a color bar at the edge of a color printing sheet. However, as will be apparent from the subsequent description herein, the principles of the invention are not limited to measurement of printed ink-on-paper.

As the light rays 210 are projected onto the object sample 212, electromagnetic radiation shown as light rays 214 will be reflected from the sample 212. As previously described in the section entitled "Background of the Invention", it is necessary to obtain quantitative measurements of this reflected light for purposes of determining the relative proportions of the light reflected from various object samples. As also previously described, it is substantially impossible to measure all of the light reflected from the sample 212. Accordingly, standard detection configurations have been developed, whereby reflected light is detected at a specific angle relative to the illumination light rays 210 projected normal to the plane of the object sample 212. More specifically, standards have been developed for detection of reflected light rays at an angle of 45° to the normal direction of the light rays 110. This angle of 45° has become a standard for reflectance measurement and is considered desirable in that this configuration will tend to maximize the density range of the measurements. In addition, however, the 45° differential also represents somewhat of a relatively normal viewing configuration of a human observer (i.e. illumination at a 45° angle from the viewer's line of sight).

For purposes of providing light detection, a spectral filter apparatus 216 is provided. The filter apparatus 216 can include a series of filters 218, 220 and 222. The filters 218, 220 and 222 are employed for purposes of discriminating the cyan, magenta and yellow spectral responses, respectively. That is, each of the filters will tend to absorb light energy at frequencies outside of the bandwidth representative of the particular color hue of the filter. For example, the cyan filter 218 will tend to absorb all light rays, except for those within the spectral bandwidth corresponding to a red hue. By detecting reflected light rays only within a particular color hue bandwidth, and obtaining an optical density measurement with respect to the same, a "figure of merit" can be obtained with respect to the quality of the object sample coloring associated with that particular color hue.

Figure 1:
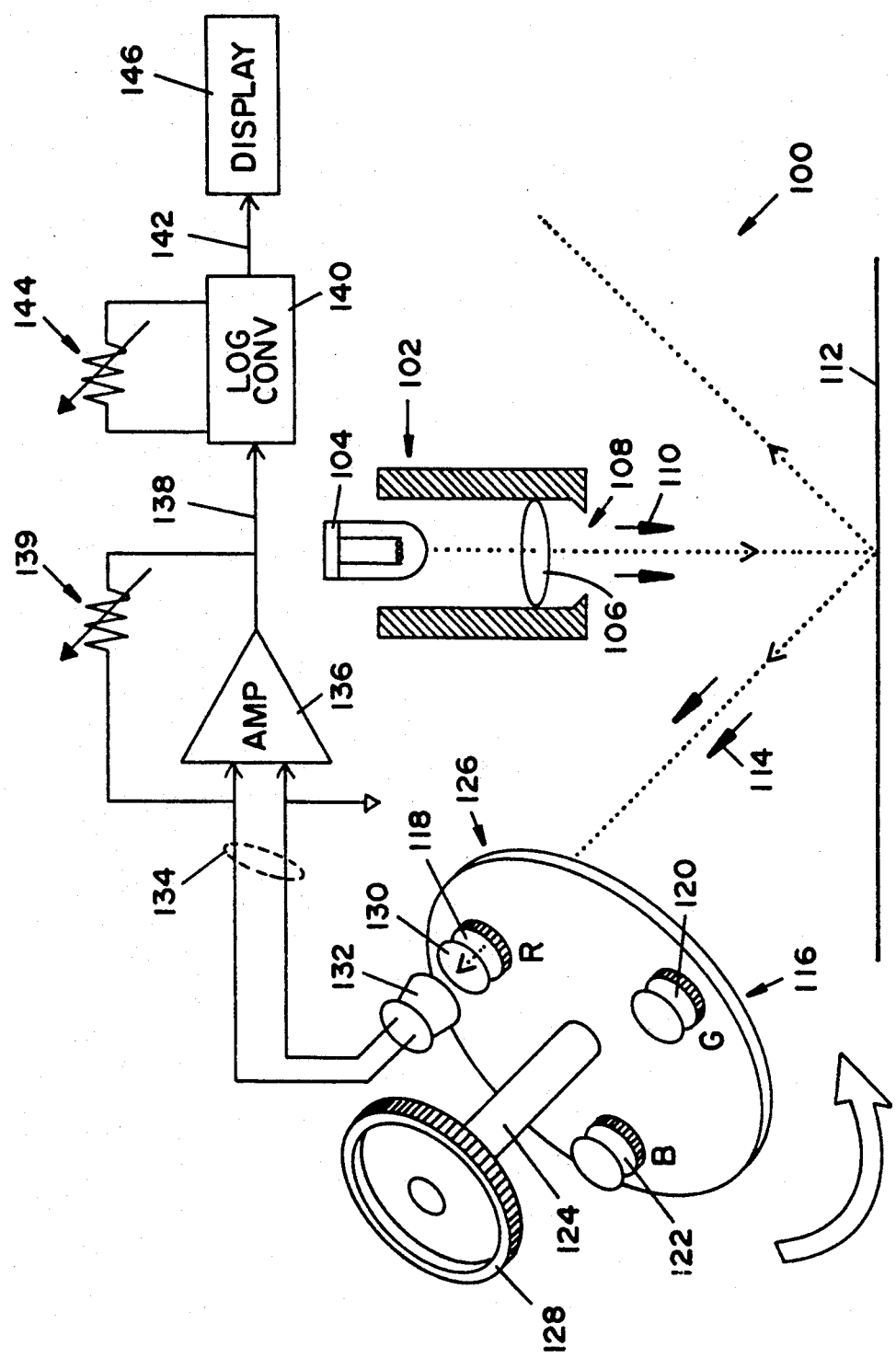
FIG. 1 is a partially schematic block diagram of a densitometer apparatus for measuring color densities.

It is apparent from the foregoing that the actual quantitative measurement of color density or reflectance is dependent in substantial part on the spectral transmittance characteristics of the filters. Accordingly, various well-known standards have been developed with respect to spectral characteristics of densitometer filters. These standards were previously described with respect to the prior art densitometer apparatus 100 illustrated in FIG. 1.

Although the filters 218, 220 and 222 are illustrated in the embodiment shown in FIG. 2 as the cyan, magenta and yellow color shades, other color shades can clearly be employed. These particular shades are considered somewhat preferable in view of their relative permanence and because they comprise the preferred shades for use in reflection densitometer calibration. However, it is apparent that different shades of red, blue and yellow, as well as entirely different colors, can be utilized with the densitometer apparatus 200 without departing from the novel concepts of the invention.

The spectral filters 218, 220 and 222 may not only comprise various shades of color, but can also be of any of several specific types of spectral response filters. For examples, the filters can comprise a series of conventional Wratten gelatin filters and infrared glass. However, various other types of filter arrangements can also be employed.

The spectral filters 218, 220 and 222 are preferably positioned at a 45° angle relative to the normal direction from the plane of the object sample 212 under test. However, unlike the densitometer configuration 100 previously described, each of the filters 218, 220 and 222 are maintained stationary and are utilized to simultaneously receive light rays reflected from the object sample 212 under test. Accordingly, it is unnecessary for the user to manually rotate or otherwise sequentially move spectral filters into receptive positions. Various types of densitometer structural configurations can be utilized to appropriately position each of the filters at the preferable 45° angular position.

As further shown in FIG. 2, the portion of the reflected light rays 214 which pass through the filters 218, 220 and 222 (shown as light rays 224, 226 and 228, respectively) impinge on receptor surfaces of photovoltaic sensor cells. The sensor cells are illustrated in FIG. 2 as sensors 232, 234 and 236 associated with the spectral filters 224, 226 and 228, respectively. The sensors 232, 234 and 236 can comprise conventional photoelectric elements adapted to detect the light rays eminating through the corresponding spectral filters. The sensors are further adapted to generate electrical currents having magnitudes proportional to the intensities of the sensed light rays. As illustrated in FIG. 2, the electrical current generated by the cyan sensor 232 in response to the detection of light rays projecting through the filter 218 is generated on line pair 238. Correspondingly, the electrical current generated by the magenta sensor 234 is applied to the line pair 240, while the electrical current generated by the yellow sensor 236 is applied as output current on line pair 242. Photoelectric elements suitable for use as sensors 236, 238 and 240 are well known in the art, and various types of commercially available sensors can be employed.

The magnitude of the electrical current on each of the respective line pairs will be proportional to the intensity of the reflected light rays which are transmitted through the corresponding spectral filter. These light rays will have a spectral distribution corresponding in part to the product of the spectral reflectance curve of the object sample 212, and the spectral response curve of the corresponding filter. Accordingly, for a particular color shade represented by the spectral response curve of the filter, the magnitude of the electrical current represents a quantitative measurement of the proportion of reflectance of the object sample 212 within the frequency spectrum of the color shade.

As further shown in FIG. 2, the sensor current output on each of the line pairs 238, 240 and 242 is applied as an input signal to one of three conventional amplifiers 244, 246 and 248. The amplifier 244 is responsive to the current output of cyan sensor 232 on line pair 238, while amplifier 246 is responsive to the sensor current output from magenta sensor 234 on line pair 240. Correspondingly, the amplifier 248 is responsive to the sensor current output from yellow sensor 236 on line pair 242. Each of the amplifiers 244, 246 and 248 provide a means for converting low level output current from the respective sensors on the corresponding line pairs to voltage level signals on conductors 250, 252 and 254, respectively. The voltage level of the signals on the respective conductors are of a magnitude suitable for subsequent analog-to-digital (A/D) conversion functions. Such amplifiers are well known in the circuit design art and are commercially available with an appropriate volts per ampere conversion ratio, bandwidth and output voltage range. The magnitudes of the output voltages on lines 250, 252 and 254 again represent the intensity of reflected light rays transmitted through the corresponding spectral filters.

Each of the voltage signal outputs from the amplifiers are applied as input signals to a conventional multiplexer 256. The multiplexer 256 operates so as to time multiplex the output signals from each of the amplifiers 244, 246 and 248 onto the conductive path 258. Timing for operation of the multiplexer 256 can be provided by means of clock signals from master clock 260 on conductive path 262. During an actual density measurement of an object sample, the densitometer 200 will utilize a segment of the resultant multiplexed signal which sequentially represents a voltage output signal from each of the amplifiers 244, 246 and 248.

The resultant multiplexed signal generated on the conductive path 258 is applied as an input signal to a conventional A/D converter 264. The A/D converter 264 comprises a means for converting the analog multiplexed signal on conductor 258 to a digital signal for purposes of subsequent processing by central processing unit (CPU) 266. The A/D converter 264 is preferably controlled by means of clock pulses applied on conductor 268 from the master clock 260. The clock pulses operate as "start" pulses for performance of the A/D conversion. The A/D converter 264 can be any suitable analog-to-digital circuit well known in the art and can, for example, comprise sixteen binary information bits, thereby providing a resolution of 64K levels per input signal.

The digital output signal from the A/D converter 264 is applied as a parallel set of binary information bits on conductive paths 270 to the central processing unit (CPU) 266. As will be described subsequently herein, the CPU 266 provides several functions associated with operation of the densitometer apparatus 200. In the embodiment described herein, the CPU 266 can be utilized to perform these functions by means of digital processing and computer programs. In addition, the CPU 266 can be under control of clock pulses generated from the master clock 260 on path 272. However, it should be emphasized that a number of the functional operations of CPU 266 could also be provided by means of discreet hardware components without departing from the scope of the novel concepts of the invention.

In part, the CPU 266 is utilized to process information contained in the digital signals from the conductive paths 270. Certain of this processed information can be generated as output signals on conductive path 276 and applied as input signals to a conventional display circuit 278. The display circuit 278 provides a means for visual display of information to the user, and can be in the form of any one of several well known and commercially available display units.

In addition to the CPU 266 receiving digital information signals from the conductive paths 270, information signals can also be manually input and applied to the CPU 266 by means of a manually accessible keyboard circuit 280. As will be described in greater detail herein, the user can supply "adjustments" to color responses by means of entering information through the keyboard circuit 280. Signals representative of the manual input from the keyboard circuit 280 are applied as digital information signals to the CPU 266 by means of conductive path 282.

The particular structural configuration and type of central processing unit 266 utilized with the densitometer apparatus 200 in accordance with the invention can comprise any one of numerous types of computer arrangements. For example, as shown in FIG. 4, the central processing unit 266 can include a conventional microprocessor 284. Although various types of well known and commercially available devices can be employed for the microprocessor 284, one typical internal configuration of a microprocessor 284 is shown in FIG. 5, and a brief and simplistic description thereof will be provided.

Referring specifically to FIG. 5, the microprocessor 284 can include an internal bus 286 which provides a means for bidirectional communication between conventional circuit components of the microprocessor 284. For example, signals can be transmitted to and received from the program counter 288, which comprise signals representative of the "next" instruction in the microcomputer memory to be executed. Communication can also be provided between the internal bus 286 and microprocessor components such as the stack pointer 290, general purpose registers 292 and arithmetic unit 294. Each of these processor components is well known to those skilled in the art of internal computer system design.

The transmission and reception of data from memories and other components of the central processing unit 266 is provided by the data bus 296 which is connected to the internal bus 286 through a conventional data buffer 298, so as to provide bidirectional communication therewith in the form of 8-digit parallel binary signals. The internal bus 286 is also connected to an address bus 300 through an address buffer 302. The microprocessor 284 can provide, for example, 16-digit parallel binary address signals on the bus 300 for directed communication between the microprocessor 284 and the various memories and other devices having signal communications through the data bus 296.

Conventional system control is provided by interconnection of the control bus 304 to timing and control circuitry 306. Communication signals from the conventional timing and control circuitry 306 can be applied to various components of the microprocessor 284 through the internal bus 286.

The microprocessor 284 can also include other conventional circuit components, including an instruction register 308. The instruction register 308 comprises a register to which the "next" instruction is stored for purposes of decoding and execution. The data within the instruction register 308 is applied to the instruction decoder 310 which comprises conventional circuitry for decoding the instruction data received from the next program location in memory. The microprocessor 284 can also include such conventional components as a flag register 312 utilized for various programming control within the processor 284.

The control bus 304 can be characterized as comprising a series of individual command signal leads. The signal leads include "transmitted" commands shown in FIG. 5 as the "read," "write," "memory" and "I/O" commands. In addition, the control bus 304 is adapted to apply certain "received" commands to the timing and control circuitry 306. These commands are symbolically shown in FIG. 5 as "receive," "wait," "reset" and "interrupt" commands. The use of these commands is well known in the field of computer system design. For example, if data is to be read from a certain address location in a memory of the central processing unit 266, "enable" signals can be applied to the "read" and "memory" command leads from the timing and control circuitry 306. Correspondingly, the address of the particular memory location to be read can be transmitted on address bus 300, while the data to be read from the particular memory location will be applied to the microprocessor 284 on data bus 296. Similarly, when data is to be applied to a particular I/O device associated with the central processing unit 266, "enable" signals can be applied on the "write" and "I/O" signal command leads from the timing and control circuitry 306. Correspondingly, the address designation of the I/O device can be applied on address bus 300, while the particular data to be transmitted to the I/O device can be applied on data bus 296. Again, the circuitry associated with microprocessor 284, and microprocessor 284 itself, are well known in the art. Any one of numerous commercially available microprocessors can be adapted for use as the microprocessor 284.

Returning again to FIG. 4, the central processing unit 266 can include memory storage elements such as the random access memory (RAM) 314. The RAM 314 is conventional in design and includes memory locations wherein data may be stored and modified during execution of program sequences. Similarly, for storage of "permanent" data or instructions wherein modifications must be made only occasionally, a conventional eraseable-programmable read only memory (EPROM) 316 is also employed. Both the RAM memory 314 and EPROM memory 316 are interconnected with the microprocessor 284 so as to allow control and address location signals to be applied on the control bus 304 and address 300, respectively. In addition, for purposes of reading data from the memories into the microprocessor 284, and for writing data into the memories, bidirectional communication is established between the RAM memory 314, EPROM memory 316 and the microprocessor 284 through data bus 296.

For purposes of intercommunication with external devices, the central processing unit 266 also includes a parallel I/O interface module 318 and a serial I/O interface module 320. The parallel interface module 318 provides a means for transmitting and receiving data signals between the microprocessor 284 and external devices which generate and receive signals in parallel format. The serial interface module 320 is utilized to interface with the external devices in a serial format.

Like the RAM memory 314 and EPROM memory 316, the interface modules 318 and 320 are interconnected with the microprocessor 284 through the control bus 304 and address bus 300 for purposes of applying control and address information data signals, respectively, to each of the modules. In addition, the interface modules 318 and 320 are interconnected to the processor 284 through data bus 296 so that data signals are bidirectionally transferable between the modules 318, 320 and processor 284. It should be emphasized that the general circuitry of the central processing unit 266 and the functional operations associated therewith are well known in the field of computer system design. Any one of numerous commercially available central processing units can be adapted for use as the CPU 266. In addition, it should also be emphasized that the CPU 266 need not specifically be of a microcomputer design. Other types of digital computers can be employed in accordance with the invention.

As previously described, known densitometer arrangements are prone to density measurement errors caused by spectral response deviations from standardized and "ideal" spectral response characteristics. Such errors can be of primary importance when performing functions such as measuring color densities of printed ink-on-paper. These known systems have no convenient means for appropriately adjusting or compensating the densitometer for spectral errors from standard spectral responses. Furthermore, these known densitometers have no convenient means for calibration in a manner which allows a user to make a second densitometer instrument match a first instrument that was used, for example, to obtain important historical printing data. It is apparent that all printing performed within one controlled environment should be measured by densitometers providing identical results.

In accordance with the invention, the densitometer apparatus 200 illustrated in FIG. 2 can be employed to overcome the foregoing problems. More specifically, the densitometer apparatus 200 can be employed to allow the user to adjust for small spectral errors by means of initially inputting certain calibration measurements through the keyboard 280. In substantial part, the entered data can comprise certain desired density values, in accordance with color reference standards or in accordance with density measurements of color reference standards derived from another theoretically correct densitometer to which the apparatus 200 is to be correlated.

Actual measurements of color reference patches can then be performed to solve for unknown constants of a set of equations representing correction or compensation factors functionally dependent on actual reflectance measurements. These correction factors can then be utilized by the apparatus 200 to compensate subsequent measurements of actual object samples.

Stated in another manner, following the calibration procedures in accordance with the invention, each measurement of color density undertaken by the user on an object sample can be subjected to a 3-color spectral analysis. The analysis can be performed by means of user-adjusted correction formulas, taking into account logarithmic density slope adjustments, zero density adjustments and color adjustments set by the user during the calibration sequence.

The principles of the invention can best be understood by describing procedures comprising an illustrative calibration sequence in accordance with the invention. The calibration sequence can employ a calibration reference card, such as the reference card 322 shown in FIG. 3. The reference card 322 can include a black reference patch 324, white reference patch 326, cyan color shade reference patch 328, magenta reference patch 330 and yellow reference patch 332.

To initiate the calibration procedure, zero density levels of the cyan, magenta, yellow and black color shades for the white reference patch 326 are first entered into the CPU 266 by means of the keyboard 280. It will be apparent that the densitometer apparatus 200 can be programmed in a manner so as to "prompt" the user for each of the manually entered values by means of the CPU 266 generating display command signals on conductive path 276, which are then applied to the visual display 278 to generate the appropriate commands.

Following entry of the appropriate data for setting the zero density levels, the CPU 266 can prompt the user (through display commands on visual display 278) for entry of cyan, magenta, yellow and black values for the black reference patch 324. As previously described, with the black reference patch 324 having a theoretically spectrally flat reflectance curve, the entry of these values can be utilized by the CPU 266 to set the slopes of the color density responses of the densitometer apparatus 200.

In accordance with the invention, the user can then be prompted to enter the cyan value for the cyan reference patch 328. This value represents the desired density readout for the cyan spectral filter path when the densitometer is made to read a cyan reference patch. Entry of this value through the keyboard 280 is utilized as subsequently described herein for purposes of computing a cyan color adjustment function. It should be noted that the appropriate cyan values to be entered for purposes of calibration procedures may differ depending on the particular type of spectral filter arrangement being employed.

Following entry of the cyan value, the user can be prompted through the display 278 to enter the desired magenta color density value for the magenta reference patch 330. Entry of this desired color density value is utilized in part to determine a magenta color adjustment function. Again, the desired color density measurement when the densitometer apparatus 200 is measuring the density of the magenta reference patch 330 is dependent in part upon the particular type of spectral filter arrangement.

Following entry of the desired cyan and magenta density values, the user can be prompted to enter the desired color density value for the yellow reference patch 332. As with entry of the cyan and magenta color density values, the desired value will correspond to the appropriate density output of the densitometer apparatus 200 when the apparatus 200 is measuring the yellow reference patch 332. Entry of the yellow color density value is utilized to determine a yellow color adjustment function.

After the foregoing data has been entered into the densitometer apparatus 200 through use of the keyboard 280, the apparatus 200 can be made to measure the color densities of each of the reference patches of reference card 322. In accordance with the principles of operation of the invention, and by way of example, the desired densitometer cyan reflectance value can be expressed as value $C_I$ in accordance with the following:

$$C_I = C f(C,M,Y) \qquad \text{(Equation 1)}$$

where f(C,M,Y) represents a function of the actual measured reflectance values for the cyan, magenta and yellow reference patches, respectively. Correspondingly, the desired density value obtained from the densitometer apparatus 200 for the cyan reference patch 328 can be expressed as $D_{CI}$ in accordance with the following:

$$D_{CI} = K_S \log_{10}\left(\frac{1}{C_I}\right) \qquad \text{(Equation 2)}$$

where $K_S$ represents an adjusted slope constant for desired cyan density at high black densities.

The function f(C,M,Y) can be characterized in part as a correction factor function for cyan color density measurements which takes into account the spectral response errors and other potential density measurement errors as previously described herein. Correction factors for reflectance and density measurements for magenta and yellow color shades can also be expressed in a manner similar to the expressions of Equations 1 and 2. Each of the correction factor functions can further be characterized as comprising a series of constants in addition to the independent variables comprising the measured reflectance values for cyan, magenta and yellow. By performing the series of measurements of the color densities and reflectances on the reference patches, and making the assumption that the unknown constants are appropriately limited in number, the actual measurements for the reference patches will provide a set of matrix equations in accordance with the correction factor functions. These matrix equations can then be solved for the unknown constants. Accordingly, referring again to Equation 1, the only unknowns will comprise the actual cyan, magenta and yellow reflectance measurements. In accordance with the invention, however, a measurement of any particular object sample under test by the densitometer apparatus 200 can provide a spectral reflectance response at the output of the multiplexer 256 for each of the cyan, magenta and yellow spectral filters. Accordingly, the output of the densitometer apparatus 200 for the cyan reflectance value during measurement of an object sample under test can be characterized as reflectance value $C_O$ and expressed as follows:

$$C_O = C f(C,M,Y) \qquad \text{(Equation 3)}$$

where C, M and Y again represent the actual cyan, magenta and yellow reflectance measurements, respectively. The appropriate output density to be displayed by the densitometer apparatus 200 through the display 278 can be expressed as $D_{CO}$ in accordance with the following:

$$D_{CO} = K_S \log_{10}\left(\frac{1}{C_O}\right) \qquad \text{(Equation 4)}$$

where $K_S$ again represents the adjusted slope constant for desired cyan density at high black densities.

The particular correction factor functions employed with a densitometer apparatus in accordance with the invention are not limited to any one specific mathematical function. It is clear that as further development is achieved in the art of densitometer and spectral filter design, new and improved functions can be developed. Furthermore, not every correction factor function may be a function of all of the actual cyan, magenta and yellow reflectance measurements.

An illustrative embodiment of one correction factor function for the cyan patch can be expressed as follows:

$$C_I = C\left(F_C + K_C \frac{M}{C} - K_1 \frac{C}{M}\right) K_2 \quad \text{(Equation 5)}$$

where $C_I$ is the desired instrument reflectance, C represents the actual cyan reflectance measurement, M represents the actual magenta reflectance measurement and Y represents the actual yellow reflectance measurement. In addition, Equation 5 shows the following constants: $K_C$ is an adjusted constant utilized to make the densitometer apparatus generate the desired cyan color density when the cyan reference patch is measured; $K_1$ represents a fixed constant utilized to make the densitometer apparatus generate the desired cyan color density when measuring color reference patches other than the cyan patch; $K_2$ represents an adjusted zero constant for the desired cyan color density to be generated by the densitometer apparatus at low densities; and $F_C$ represents an adjustment constant to make the following mathematical formula equal to 1 when measuring the black reference patch 324:

$$F_C + K_C \frac{M}{C} - K_1 \frac{C}{M} \quad \text{(Equation 6)}$$

Again, the desired densitometer apparatus output for color density for the cyan patch can be characterized in a manner identical to Equation 2.

Similar correction factor functional equations can also be developed for the magenta and yellow reference patches. When measurements are made on the reference patches of the reference card 322 by utilization of the densitometer apparatus 200 as previously described, a set of matrix equations represented in part by Equations 2, 5 and 6 can be developed. The central processing unit 266 can then be employed to solve for the unknown constants.

A representative operational sequence for calibration of the densitometer apparatus 200 in accordance with the foregoing description is shown in FIG. 6. Advantageously, and further in accordance with the invention, the calibration procedure allows the densitometer apparatus to be calibrated so as to measure the same as any other densitometer (commonly referred to as inter-instrument agreement). To obtain inter-instrument agreement, the cyan, magenta, yellow and black density values of white and black reference patches can be measured and recorded, utilizing the particular densitometer apparatus which the user wishes to correlate with the densitometer apparatus 200. The cyan, magenta and yellow density values for the cyan, magenta and yellow patches, respectively, can then be measured and recorded, utilizing the same densitometer apparatus. These values can then be entered into the densitometer apparatus 200 as previously described.

As apparent from the foregoing, a densitometer apparatus in accordance with the invention provides a means for measuring printed materials utilizing 3-color response receptors to simultaneously generate information regarding all measurements. This information is utilized for the purpose of adjusting each measurement by the use of correction factor functions which relate the 3-color reflectances to the type of sample measured. In this manner, more than one densitometer can be made to measure color printed material in a manner identical to other densitometers. To achieve this functional advantage, densitometer apparatus in accordance with the invention can utilize color printed material combined with data input from a user for the purpose of adjusting the densitometer color density response.

Densitometer apparatus in accordance with the invention also employ the use of a keyboard and a visual display for purposes of allowing the user to conveniently enter color response corrections into the central processing unit of the densitometer.

Densitometer apparatus in accordance with the invention are also advantageous in that the capability of providing correction required by small spectral response errors can reduce the actual number of requisite spectral filter types. Experimentation has shown that the number of conventional and well known spectral filter types can be reduced at least from four to two types.

It must be emphasized that the principles of the invention are not limited to the specific densitometer apparatus 200 described herein. For example, other types of circuit components can be employed. Instead of the use of a keyboard such as the keyboard 280 described herein, entry systems employing circuit components such as potentiometers could be utilized. Furthermore, the principles of the invention are not limited to any specific correction factor functions or specific constants.

Still further, the calibration procedure described herein in accordance with the invention is not necessarily limited to a 3-color calibration or to the use of cyan, magenta and yellow spectral references. A different number of colors and different color shades could be employed without departing from the novel concepts of the invention. It will be further apparent to those skilled in the art that additional modifications and variations of the above-described illustrative embodiment of the invention may be effected without departing from the spirit and scope of the novel concepts of the invention.

The embodiments of the invention in which an exclusive property or privilege is claimed are defined as follows:

1. A densitometer system adapted for measuring color characteristics of a substantially opaque object sample under test, the system comprising:

light source means for generating light rays and directing the same onto the object sample;

spectral filter means positioned at a predetermined angle relative to the direction of object illumination by the light source, and responsive to light rays reflected from the object sample so as to discriminate a predetermined color shade set of spectral responses of the reflected light rays;

detection means responsive to the light rays transmitted through the spectral filter means for generating on separate paths signals representative of the intensity of the transmitted light rays;

multiplexing means connected to the detection means for time multiplexing the signals on the separate paths;

processing means connected to the multiplexing means for processing the multiplexed signals;

input means connected to the processing means for providing user input to the densitometer; and the processing means comprises means for generating solutions to correction factor functions relating a desired reflectance measurement to an actual reflectance measurement for each of the spectral filter color shades, wherein the correction factor functions are each a function of at least two of the actual reflectance measurements of the spectral filter color shades.

2. In a densitometer system adapted for measuring color characteristics for a plurality of color shades of a substantially opaque object sample under test, and comprising light source means for generating light rays and directing the same onto the object sample, means responsive to reflected light rays reflected from the object sample for generating measured signals representative of the intensities of the reflected light rays, and processing means for processing the measured signals so as to generate data signals indicative of the color characteristics, the improvement wherein:

the processing means comprises means for generating solutions to at least one correction factor function relating desired color characteristic measurements to actual color characteristic measurement readings for a color shade, wherein the correction factor function is a function of the measured signals representative of intensities of the reflected light rays for at least two of the plurality of color shades.

3. A densitometer system in accordance with claim 2 characterized in that the system further comprises input means connected to the processing means for receiving user input data representative of desired color characteristic readings of reference samples.

4. A densitometer system in accordance with claim 2 characterized in that:

the object samples under test comprise a plurality of reference samples of various of a plurality of color shades, wherein a first one of the reference samples is a substantially reflective color shade, and a second one of the reference samples is a color shade of relatively high absorptance; and the system further comprises input means connected to the processing means for receiving first user input data representative of desired density levels of a first set of color shades for the first reference sample.

5. A densitometer system in accordance with claim 4 characterized in that the input means is further adapted to receive second user input data representative of desired density levels of a second set of color shades for the second reference sample; and the processing means is responsive to the first user input data and second user input data for setting slopes of color density responses of the densitometer system.

6. A densitometer system in accordance with claim 4 characterized in that the input means is further adapted for receiving third user input data, representative of desired density readings for specific color shades when the densitometer system is made to read the reference samples of like color shades.

7. A densitometer system in accordance with claim 4 characterized in that the first one of the reference samples is a white reference sample, the second one of the reference samples is a black reference sample and the reference samples comprise cyan, magenta and yellow reference samples.

8. A densitometer system in accordance with claim 2 characterized in that the correction factor function comprises a series of constants and independent variables, where the independent variables comprise values of the measured signals representative of intensities of the reflected light rays for at least two of the plurality of color shades.

9. A densitometer system in accordance with claim 2 characterized in that:

the system further comprises output means connected to the processing means for providing to the user output data representative of color characteristic data for the object samples under test; and the processing means comprises means for generating the output data in the form of the value of the actual color characteristic measurements for a particular color shade, multiplied by the correction factor function for the particular color shade, thereby providing error correction for the actual color characteristic measurements.

10. A densitometer system in accordance with claim 2 characterized in that the means repsonsive to reflected light rays reflected from the object samples for generating measured signals representative of intensities of the reflected light rays comprises:

spectral filter means positioned at a predetermined angle relative to the direction of object illumination by the light source, and responsive to light rays reflected from the object sample so as to discriminate a predetermined color shade set of spectral responses of the reflected light rays;

detection means responsive to the light rays transmitted through the spectral filter means for generating on separate paths signals representative of the intensities of the transmitted light rays; and multiplexing means connected to the detection means for time multiplexing the signals on the separate paths.

11. A densitometer system adapted for measuring color characteristics of a substantially opaque sample under test, and for proving error correction and calibration through utilization of a set of reference samples, the system comprising:

a light source for generating light rays and directing the same onto the reference samples;

a set of spectral filters positioned at a predetermined angle relative to the direction of object illumination by the light source, and responsive to light rays reflected from the reference sample so as to discriminate a predetermined color shade set of spectral responses of the reflected light rays;

a set of sensors responsive to the light rays transmitted through the spectral filters for generating on separate paths signals representative of the intensities of the transmitted light rays;

a multiplexer connected to the sensors for time multiplexing the signals representative of the intensities of the transmitted light rays;

processing means connected to the multiplexer for processing the multiplexed signals;

input means connected to the processing means for providing user input to the densitometer system; and the processing means comprises means for generating a separate correction factor for each of the color shades, wherein each of the correction factors comprises a series of constants and a set of independent variables, and further wherein the independent variables comprise actual reflectance measurements for at least two of the color shades.

12. A densitometer system in accordance with claim 11 characterized in that the series of constants comprises:
   a first constant for making the densitometer system generate a desired color density value for a particular color shade when the reference sample of the same color shade is measured;
   a second constant for making the densitometer system generate a desired color density value for the particular color shade when reference samples other than reference samples of the particular color shade are measured;
   a third constant for making the densitometer system generate a desired color density value for the particular color shade when the densitometer system is measuring samples of relatively low color densities; and
   a fourth constant for making the mathematical formula $(F_c + K_c (M/C) - K_1 (C/M))$ substantially equal to one when the densitometer system is measuring a reference sample of a substantially black color shade, where $K_c$ is the first constant, $K_1$ is the second constant, $K_2$ is the third constant, $F_c$ is the fourth constant, M is an actual color characteristic measurement of a reference sample of one of the color shades, and C is an actual color characteristic measurement of a reference sample of another of the color shades.

13. A method adapted for use in a densitometer system for measuring color characteristics of object samples under test, the method being specifically adapted for error correction through utilization of a plurality of reference samples of varying color shades, the method comprising the steps of:
   entering input data into the densitometer system representative of desired color characteristic readings for the reference samples;
   generating light rays and directing the same onto the reference samples;
   generating measured signals representative of intensities of reflected light rays reflected from the reference samples;
   processing the measured signals so as to generate data signals indicative of the color characteristics of the reference samples; and
   generating solutions to at least one correction factor function relating desired color characteristic measurements to actual color characteristic measurement readings for a color shade, wherein the correction factor function is a function of the measured signals representative of intensities of the reflected light rays for at least two of the plurality of color shades.

14. A method in accordance with claim 13 characterized in that the entry of input data comprises:
   entering input data representative of desired color characteristic readings of a first set of the color shades for a first one of the reference samples;
   entering input data representative of desired color characteristic readings of a second set of the color shades for a second one of the reference samples; and
   entering input data representative of color characteristic readings for specific color shades which are desired when the densitometer system is made to read reference samples of like color shades.

15. A method in accordance with claim 14 characterized in that the first one of the reference samples is a color shade of relatively low density.

16. A method in accordance with claim 14 characterized in that the second one of the reference samples is a color shade of relatively high density.

17. A method in accordance with claim 14 characterized in that the method further comprises the steps of setting slopes of color density responses of the densitometer system in accordance with the input data representative of desired color characteristic readings of the first and second sets of color shades.

18. A method in accordance with claim 13 characterized in that the correction factor function comprises a series of constants and independent variables, wherein the independent variables comprise values of the measured signals representative of the intensities of reflected light rays reflected from the reference samples.

19. A method in accordance with claim 13 characterized in that:
   the plurality of reference samples comprises first, second, third, fourth and fifth reference samples having first, second, third, fourth and fifth color shades, respectively, and wherein the first color shade is a substantially reflective color shade and the second color shade is a color shade of relatively high absorptance; and
   the entry of input data comprises:
      entering input data into the densitometer system representative of desired zero density levels of the second, third, fourth and fifth color shades for the first reference sample;
      entering input data into the densitometer system representative of density levels of the second, third, fourth and fifth color shades for the second reference sample;
      entering input data into the densitometer system representative of the desired density reading for the third color shade when the densitometer system is made to read the third reference sample;
      entering input data into the densitometer system representative of the desired density reading for the fourth color shade when the densitometer system is made to read the fourth reference sample; and
      entering input data into the densitometer system representative of the desired density reading for the fifth color shade when the densitometer system is made to read the fifth reference sample.

20. A method in accordance with claim 13 characterized in that the method further comprises the steps of:
   generating measured signals representative of intensities of reflected light rays reflected from an object sample under test;
   processing the measured signals so as to generate data signals indicative of the actual color characteristic readings of the object sample under test; and
   generating output data in the form of corrected color characteristic readings, wherein the corrected readings comprise the values of the actual color characteristic readings multiplied by the correction factor function.

* * * * *